United States Patent
Lorenz et al.

(10) Patent No.: US 7,605,292 B2
(45) Date of Patent: Oct. 20, 2009

(54) METHOD FOR THE SEPARATION OF POLYMERIC BY-PRODUCTS FROM 1,4-BUTYNEDIOL

(75) Inventors: Rudolf Erich Lorenz, Ludwigshafen (DE); Rolf Pinkos, Bad Duerkheim (DE); Michael Steiniger, Neustadt (DE); Gerd Schaefer, Monsheim (DE); Thomas Danner, Erpolzheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 12/351,253

(22) Filed: Jan. 9, 2009

(65) Prior Publication Data

US 2009/0187050 A1    Jul. 23, 2009

Related U.S. Application Data

(63) Continuation of application No. 12/065,311, filed as application No. PCT/EP2006/065591 on Aug. 23, 2006, now Pat. No. 7,538,254.

(30) Foreign Application Priority Data

Sep. 6, 2005    (DE) ........................ 10 2005 042 184

(51) Int. Cl.
    *C07C 29/17* (2006.01)
(52) U.S. Cl. .................. 568/861; 568/857; 568/856
(58) Field of Classification Search .................. 568/861, 568/857, 856
    See application file for complete search history.

(56) References Cited

U.S. PATENT DOCUMENTS

| 4,153,578 A | 5/1979 | De Thomas et al. |
| 4,288,640 A | 9/1981 | Schuster et al. |
| 4,294,998 A | 10/1981 | Copelin |
| 5,068,468 A | 11/1991 | Schossig et al. |
| 5,973,213 A | 10/1999 | Flood et al. |
| 6,420,615 B1 | 7/2002 | Chaudhari et al. |

FOREIGN PATENT DOCUMENTS

| DE | 1 941 633 | 8/1969 |
| DE | 20 40 501 | 8/1970 |
| DE | 272 644 | 10/1989 |
| DE | 44 32 581 | 3/1996 |
| DE | 195 08 751 | 9/1996 |
| DE | 195 35 450 | 3/1997 |
| DE | 196 25 189 | 10/1997 |
| EP | 0 319 208 | 11/1988 |
| EP | 1 207 146 | 5/2002 |
| GB | 13 62 071 | 7/1974 |

OTHER PUBLICATIONS

Weissermel, Arpe. Industrielle Organsche Chemie, 5$^{th}$ Ed., pp. 110-111, 1998.
Ullmanns Encyclopadie der Techn. Chemie, 4$^{th}$ Ed. pp. 558-569, 1977.

*Primary Examiner*—Elvis O Price
(74) *Attorney, Agent, or Firm*—Oblon, Spivak, McClelland, Maier & Neustadt, L.L.P.

(57) ABSTRACT

The present invention relates to a process for purifying 1,4-butynediol, which comprises compressing 1,4-butynediol to from 50 to 1500 bar, depressurizing it, waiting for phase separation to occur after depressurization and separating off the bottom phase, and a process for the hydrogenation of 1,4-butynediol to 1,4-butenediol and 1,4-butanediol using the purified 1,4-butynediol.

21 Claims, No Drawings

METHOD FOR THE SEPARATION OF POLYMERIC BY-PRODUCTS FROM 1,4-BUTYNEDIOL

CROSS-REFERENCE TO RELATED APPLICATION

This application is a continuation of U.S. application Ser. No. 12/065,311, filed Feb. 29, 2008, now U.S. Pat. No. 7,538,254 which is a 371 of PCT/EP06/065591, filed on Aug. 23, 2006, and claims priority to German Application No. 102005042184.9, filed Sep. 6, 2005

DESCRIPTION

The invention relates to a process for purifying 1,4-butynediol by removing impurities in the form of polymeric by-products and catalyst constituents and also a process for preparing 1,4-butenediol and 1,4-butanediol by hydrogenation of the purified 1,4-butynediol, which comprises the removal of polymeric by-products. The synthesis of 1,4-butynediol from acetylene and formaldehyde is carried out widely in industry and has been described, for example, in K. Weissermel, H.-J. Arpe, Industrielle organische Chemie, 5th edition, 1998, Wiley-VCH, pages 110 and 111. In addition to copper, the catalysts customarily used may, if appropriate, comprise bismuth and silicates (hereinafter referred to as $SiO_2$) or aluminum oxide. During the synthesis of 1,4-butynediol, the formation of oligomeric or polymeric substances (hereinafter referred to as cuprenes) occurs as secondary reaction. These cuprenes usually go together with soluble and insoluble constituents of the catalyst used into the hydrogenation stage in which 1,4-butenediol is formed first and can be hydrogenated in a further hydrogenation step to form the more important, compared to 1,4-butenediol, intermediate 1,4-butanediol.

The hydrogenation of 1,4-butynediol to 1,4-butanediol has been carried out for decades and has been described widely. Thus, U.S. Pat. No. 5,068,468 discloses the hydrogenation of 1,4-butanediol over solid supported nickel-copper catalysts, while U.S. Pat. No. 4,153,578 describes a two-stage process for hydrogenating 1,4-butynediol over suspended Raney nickel-molybdenum catalyst at a pressure of 21 bar. DD-A 272 644 discloses the suspension hydrogenation of aqueous butynediol over nickel-$SiO_2$ catalysts and general hydrogenation processes which can be applied, inter alia, to 1,4-butynediol are known from EP-B 0 319 208, DE-A 19 41 633 and DE-A 20 40 501.

Cuprenes and catalyst constituents from the butynediol synthesis interfere in its hydrogenation to 1,4-butenediol or 1,4-butanediol and significantly impair the hydrogenation result. Thus, cuprenes deposit on the catalyst and hinder contact of butynediol with the catalyst surface, as a result of which the reaction becomes slower. Catalyst components such as copper, bismuth and/or $SiO_2$ likewise deposit on the catalyst and thus change the catalyst activity and selectivity.

Even without removal of the catalyst from the reactor, these disadvantageous effects can be followed by monitoring the formation of the by-product butanol, since its formation is accelerated by the abovementioned catalyst poisons.

The simple purification of 1,4-butynediol, e.g. by filtration, is not readily possible since the cuprenes and $SiO_2$, in particular, are partly present in colloidal or very finely dispersed form and thus quickly block conventional filters, so that the filters either have to be continually replaced or be backflushed in a complicated procedure.

It is an object of the invention to provide a simple economical process by means of which the components which are undesirable in the hydrogenation stage can be removed from 1,4-butynediol to give a purified 1,4-butynediol from which 1,4-butenediol or 1,4-butanediol can be obtained with high selectivity and with a good catalyst operating life by hydrogenation.

It has now surprisingly been found that a process which comprises compressing technical-grade 1,4-butynediol to from 50 to 1500 bar, depressurizing it, waiting for phase separation to occur after depressurization and then separating off the bottom phase leads to removal of the components which are undesirable in the hydrogenation stage from 1,4-butynediol and makes it possible to obtain 1,4-butenediol and 1,4-butanediol by hydrogenation, each with high selectivity and with a good catalyst operating life. In the present patent application, technical-grade 1,4-butynediol is 1,4-butynediol which has been prepared from acetylene and formaldehyde over customary catalysts and has not yet been purified, for example, by distillation, and generally comprises from 10 to 70% by weight of butynediol, preferably from 30 to 60% by weight of butynediol, from 0.2 to 4% by weight of propynol, 0.1-2% by weight of formaldehyde and from 1 to 2000 ppm, preferably from 3 to 500 ppm, particularly preferably from 10 to 200 ppm, of cuprenes and catalyst constituents and also <0.1% of other impurities.

1,4-Butynediol is compressed to from 50 to 1500 bar by means of commercial pumps. The higher the compression pressure, the more successful is the process of the invention. This pressure is preferably above 150 bar, particularly preferably above 250 bar. The time for which the 1,4-butynediol is in compressed form is not critical per se. This period of compression can be, for example, from 0.5 seconds to 5 hours.

After compression, the 1,4-butynediol is depressurized, preferably to ambient pressure (atmospheric pressure). However, it is also possible for it to be depressurized to subatmospheric pressure, for example in the region of 0.5 bar, or to a moderate superatmospheric pressure up to 10 bar.

The 1,4-butynediol is preferably depressurized through high-pressure homogenization devices known to those skilled in the art in the form of orifice plates or nozzles, for example single-stage or two-stage orifice homogenizers, flat nozzles or microfluidizers, with the use of orifice plates being preferred. As a person skilled in the art knows, the size of the orifice plate is to be selected as a function of the pressure and throughput. At pressures up to 1000 bar, an orifice plate having an orifice diameter of 0.4 mm is particularly preferred and an orifice plate having an orifice diameter of 0.2 mm is particularly preferred at from 1000 to 1500 bar.

After depressurization, the occurrence of phase separation is awaited. Here, it is advantageous to introduce the 1,4-butynediol into a calming zone. The calming zone can be, for example, a tank or preferably a tank having a conical outlet. The mean residence time of the 1,4-butynediol in the calming zone, corresponding to the time to occurrence of phase separation, is generally from one hour to 5 days, preferably from 5 hours to 3 days and particularly preferably from 10 hours to 30 hours.

During storage in the calming zone, two phases are formed and these are then separated from one another using methods known per se for this purpose, e.g. by decantation or centrifugation.

The heavier (bottom) phase comprises predominantly the cuprenes and also considerable amounts of copper-, bismuth- or $SiO_2$-comprising, undesirable catalyst components. This bottom phase is either passed to disposal, e.g. incineration, or can be treated beforehand, e.g. by distillation, to separate off residual 1,4-butynediol which can be recirculated to the process of the invention. The upper phase which has been largely freed of cuprenes and undesirable catalyst constituents is passed to the hydrogenation to form 1,4-butenediol or 1,4-butanediol.

The purification process of the invention is generally carried out at temperatures of from 10 to 130° C., preferably from 20 to 110° C., particularly preferably from 40 to 100° C., and can be carried out batchwise or fully continuously, with a continuous process being preferred.

In addition, the present invention provides a process for the hydrogenation of 1,4-butynediol to 1,4-butenediol and preferably to 1,4-butanediol, in which 1,4-butynediol which has been purified by the process of the invention is used.

The hydrogenation of 1,4-butynediol is known per se and is preferably carried out in the liquid phase over fixed-bed and/or suspended catalysts. The hydrogenation can be carried out to the stage of 1,4-butanediol but also only to the stage of 1,4-butenediol.

The hydrogenation of purified 1,4-butynediol is carried out using catalysts which are able to hydrogenate C-C triple and double bonds to single bonds. They generally comprise one or more elements of transition group I, VI, VII or VIII of the Periodic Table of the Elements, preferably the elements copper, chromium, molybdenum, manganese, rhenium, iron, ruthenium, cobalt, nickel, platinum and palladium. Particular preference is given to using catalysts which comprise at least one element selected from among copper, chromium, molybdenum, iron, nickel, platinum and palladium.

The metal content of these catalysts is generally 0.1-100% by weight, preferably 0.2-95% by weight, particularly preferably 0.5-95% by weight.

The catalyst preferably further comprises at least one element selected from among the elements of main groups II, III, IV and VI, transition groups II, III, IV and V of the Periodic Table of the Elements and the lanthanides as promoter to increase the activity.

The promoter content of the catalyst is generally up to 5% by weight, preferably 0.001-5% by weight, particularly preferably 0.01-3% by weight.

As catalysts, it is possible to use precipitated catalysts, supported catalysts or Raney-type catalysts whose preparation is described, for example, in Ullmanns Encyclopädie der technischen Chemie, 4th edition, 1977, volume 13, pages 558-665.

As support materials, it is possible to use aluminum oxides, titanium oxides, zirconium dioxide, silicon dioxide, clay minerals, e.g. montmorillonites, silicates such as magnesium silicates or aluminum silicates, zeolites and activated carbon. Preferred support materials are aluminum oxides, titanium dioxides, silicon dioxide, zirconium dioxide and activated carbon. Of course, it is also possible for mixtures of various support materials to serve as support for catalysts which can be employed in the process of the invention.

These catalysts can be used either as shaped catalyst bodies, for example as spheres, cylinders, rings, spirals, or in the form of powders.

Suitable Raney-type catalysts are, for example, Raney nickel, Raney copper, Raney cobalt, Raney nickel/molybdenum, Raney nickel/copper, Raney nickel/chromium, Raney nickel/chromium/iron or rhenium sponge. Raney nickel/molybdenum catalysts can be prepared, for example, by the process described in U.S. Pat. No. 4,153,578. However, these catalysts are also marketed by, for example, Degussa, 63403 Hanau, Germany. A Raney nickel-chromium-iron catalyst is marketed, for example, by Degussa under the trade name catalyst type 11 112 W®.

When precipitated or supported catalysts are used, these are reduced at from 150 to 500° C. in a stream of hydrogen or hydrogen/inert gas at the beginning of the reaction. This reduction can be carried out directly in the synthesis reactor. If the reduction is carried out in a separate reactor, the surface of the catalysts can be passivated by means of oxygen-comprising gas mixtures at 30° C. before removal from the reactor. The passivated catalysts can in this case be activated at 180° C. in a stream of nitrogen/hydrogen in the synthesis reactor prior to use or can be used without activation.

The catalysts can be used in a fixed bed or in suspension. If the catalysts are present in the form of a fixed bed, the reactor is not operated in the usual downflow mode but instead with an upward-directed cocurrent of liquid and gas so that the liquid and not the gas is present as continuous phase.

When suspended catalysts are used, they generally have a particle size of 0.1-500 μm, preferably from 0.5 to 200 μm, particularly preferably from 1 to 100 μm.

If the process is carried out using suspended catalysts and packed bubble columns, an upward-directed cocurrent of liquid and gas in which the liquid and not the gas is present as continuous phase is likewise employed. The ratio of amount of gas leaving the reaction vessel and amount of gas fed in is, both when using fixed-bed reactors and when using packed bubble columns and a catalyst suspended in the reaction medium, from 0.99:1 to 0.4:1.

The ratio of amount of gas leaving the reaction vessel and amount of gas fed in which is to be adhered to according to the invention in the case of fixed-bed reactors and in the case of catalysts suspended in the reaction medium in packed bubble columns can be set in a simple manner either by metering in the appropriate amount of hydrogen as fresh gas or, preferably, recirculating recycle gas and replacing only the hydrogen lost by chemical consumption and in the offgas by fresh hydrogen.

The molar ratio of hydrogen to 1,4-butynediol in the reactor is at least 3:1, preferably from 4:1 to 100:1.

The process of the invention is carried out over fixed-bed catalysts in the gas recycle mode, i.e. the gas leaving the reactor is recirculated, if appropriate after being supplemented with fresh hydrogen, via a compressor to the reactor. It is possible for the total amount of recycled gas or part thereof to be circulated via a jet compressor. In this preferred embodiment, the recycled gas compressor is replaced by an inexpensive nozzle. The work of compression is introduced via the liquid which is likewise circulated. The increase in the pressure of the liquid required for operating the jet compressor is about 3-5 bar.

Suitable reactors for carrying out the process of the invention using a catalyst suspended in the reaction medium are jet nozzle reactors, stirred tanks and bubble columns with packing having a packing surface area of at least 500 m$^2$/m$^3$, preferably from 1000 m$^2$/m$^3$ to 2000 m$^2$/m$^3$. Various types of jet nozzle reactors can be employed as long as they have a sufficiently high energy input, on the basis of experience above 2 kW/m$^3$, to ensure the high mass transfer from the gas phase to the liquid with the suspended catalyst particles which is essential for the invention. Jet nozzle reactors equipped with a momentum exchange tube are particularly useful. A type of jet nozzle reactor which is widespread in industry is, for example, the reactor described in EP-A 0 419 419. At energy inputs of from 3 to 5 kW/m$^3$, separation of the gas phase in simple separators is still possible without having to use additional apparatuses such as foam centrifuges or cyclones when this reactor is employed.

Stirred tanks are suitable for carrying out the process of the invention only when the energy input is in the range from 2 to 10 kW/m$^3$.

Jet nozzle reactors with suspended catalysts require energy inputs per unit volume of more than 2 kW/m$^3$, preferably 3-5 kW/m$^3$.

1,4-Butanediol is employed in large quantities in industry, for example in the production of THF or as diol component in polyesters.

EXAMPLES

The process of the invention is illustrated by the following examples. Unless indicated otherwise, technical-grade 1,4-butynediol in the form of a 54% strength by weight aqueous solution was used. The percentages reported for the reaction product mixtures in the examples are, unless indicated otherwise, percentages by weight calculated on a water-free basis and determined by gas chromatography.

Comparative Example

Technical-Grade 1,4-butynediol 190 ml of an Ni catalyst as described in example 1 of U.S. Pat. No. 5,068,468 were introduced into a hydrogenation reactor having a length of 1.2 m. Technical-grade 1,4-butynediol in the form of a 54% strength by weight aqueous solution was fed into the reactor at a feed rate of 100 g/h. Hydrogenation was carried out for 2 weeks at a temperature of 140° C., a hydrogen pressure of 200 bar and a liquid circulation of 800 ml/h.

Within the time of the experiment (2 weeks), the butynediol conversion was always quantitative. The average increase in n-butanol was about 0.06% per day. After the catalyst was removed from the reactor, solid deposits were present on the catalyst. The yield of 1,4-butanediol, based on butynediol used, was 98.3% by weight at the beginning but was reduced by 0.06% by weight each day.

Example 1

Purification of 1,4-butynediol

Purification:

Technical-grade butynediol of the composition reported in the comparative experiment was compressed to 1000 bar at 50° C. by means of a high-pressure pump for one second and subsequently depressurized immediately through the orifice plate (0.2 mm diameter). After depressurization through the orifice plate, the butynediol which had been purified in this way was fed to the hydrogenation reactor.

Hydrogenation:

The hydrogenation was carried out in a manner analogous to the comparative example using the 1,4-butynediol which had been prepurified according to the invention. The average increase in n-butanol was only about 0.04% per day. After removal of the catalyst from the reactor, no deposits were found. The yield of 1,4-butanediol, based on butynediol used, was 98.3% by weight at the beginning and was reduced by 0.04% by weight each day.

The invention claimed is:

1. A process for making 1,4-butanediol, 1,4-butenediol, or a mixture thereof, comprising:

purifying a mixture comprising 1,4-butynediol by a process comprising:
compressing said mixture to a pressure ranging from 50 to 1500 bar;
depressurizing said mixture;
phase-separating said mixture; and
removing a bottom phase of said mixture to obtain purified 1,4-butynediol; and
reacting said purified 1,4-butynediol with hydrogen in the presence of a catalyst.

2. The process according to claim 1 for preparing 1,4-butenediol.

3. The process according to claim 1 for preparing 1,4-butanediol.

4. The process according to claim 1, wherein said catalyst comprises at least one metal selected from the group consisting of copper, chromium, molybdenum, manganese, rhenium, iron, ruthenium, cobalt, nickel, platinum, and palladium.

5. The process according to claim 4, wherein said catalyst comprises at least one metal element selected from the group consisting of copper, chromium, iron, nickel, platinum, and palladium.

6. The process according to claim 4, wherein said at least one metal is present in an amount ranging from 0.1-100% by weight of said catalyst.

7. The process according to claim 4, wherein said at least one metal is present in an amount ranging from 0.2-95% by weight of said catalyst.

8. The process according to claim 4, wherein said at least one metal is present in an amount ranging from 0.5-95% by weight of said catalyst.

9. The process according to claim 4, wherein said catalyst further comprises at least one promoter selected from the group consisting of a main group II element, a main group III element, a main group IV element, a main group VI element, a transition group II element, a transition group III element, a transition group IV element, a transition group V element, and a lanthanide.

10. The process according to claim 9, wherein said at least one promoter is present in an amount of at most 5% by weight of said catalyst.

11. The process according to claim 9, wherein said at least one promoter is present in an amount ranging from 0.001-5% by weight of said catalyst.

12. The process according to claim 9, wherein said at least one promoter is present in an amount ranging from 0.01-3% by weight of said catalyst.

13. The process according to claim 1, wherein a molar ratio of hydrogen to purified 1,4-butynediol is at least 3:1.

14. The process according to claim 1, wherein said purifying occurs at a temperature ranging from 10 to 130° C.

15. The process according to claim 1, wherein said compressing occurs at a pressure ranging from 150 to 1500 bar.

16. The process according to claim 1, wherein said compressing occurs for 0.5 seconds to 5 hours.

17. The process according to claim 1, wherein said catalyst is in the form of a precipitated catalyst, a supported catalyst, or a Raney catalyst.

18. The process according to claim 1, wherein said catalyst is in the form of a support catalyst and comprises at least one support selected from the group consisting of an aluminum oxide, a titanium oxide, zirconium dioxide, silicon dioxide, a montmorillonite, a magnesium silicate, an aluminum silicate, a zeolite, and activated carbon.

19. The process according to claim 18, wherein said catalyst comprises at least one selected from the group consisting of an aluminum oxide, a titanium dioxide, silicon dioxide, zirconium dioxide, and activated carbon.

20. The process according to claim 1, wherein said catalyst is present in a suspension.

21. The process according to claim 20, wherein a particle size of said catalyst ranges from 0.1 to 500 μm.

* * * * *